United States Patent
Takada et al.

(10) Patent No.: US 6,938,494 B2
(45) Date of Patent: Sep. 6, 2005

(54) LOAD TEST MACHINE

(75) Inventors: Susumu Takada, Saitama (JP); Keiichi Furuya, Saitama (JP)

(73) Assignee: Kabushiki Kaisha Saginomiya Seisakusho, Tokyo (JP)

( * ) Notice: Subject to any disclaimer, the term of this patent is extended or adjusted under 35 U.S.C. 154(b) by 0 days.

(21) Appl. No.: 10/750,779

(22) Filed: Jan. 2, 2004

(65) Prior Publication Data
US 2004/0139804 A1 Jul. 22, 2004

(30) Foreign Application Priority Data
Jan. 16, 2003 (JP) ........................................ 2003-008120

(51) Int. Cl.[7] .............................. G01B 5/30; G01B 7/16; G01L 1/00; G01N 3/00
(52) U.S. Cl. ........................................................ 73/760
(58) Field of Search .......................... 73/781, 833, 760, 73/12.01, 826, 856, 816, 49.4, 799, 150 A, 794

(56) References Cited
U.S. PATENT DOCUMENTS

| | | | | |
|---|---|---|---|---|
| 4,478,086 A | * | 10/1984 | Gram | 73/781 |
| 4,721,000 A | * | 1/1988 | Scanlon | 73/833 |
| 4,823,473 A | * | 4/1989 | McMahon | 33/787 |
| 4,869,112 A | * | 9/1989 | Gram et al. | 73/856 |
| 4,885,941 A | * | 12/1989 | Vardoulakis et al. | 73/794 |
| 4,895,027 A | * | 1/1990 | Manahan, Sr. | 73/799 |
| 5,685,193 A | * | 11/1997 | Hurtubise et al. | 73/150 A |

\* cited by examiner

*Primary Examiner*—Max Noori
*Assistant Examiner*—Octavia Davis
(74) *Attorney, Agent, or Firm*—Reising, Ethington, Barnes, Kisselle, P.C.

(57) ABSTRACT

A load test machine includes a base block, at least a pair of posts rising from the base block, a cross head spanning between the pair of posts, and an actuator mounted on the base block or the cross head. The actuator is able to apply a load on a test piece positioned between the cross head and the base block. The cross head is secured to each of the posts via an elastic member, and the elastic member is constructed to be changeable in its jointing position with the cross head or with each of the posts to change a resonance frequency of the test machine.

12 Claims, 7 Drawing Sheets

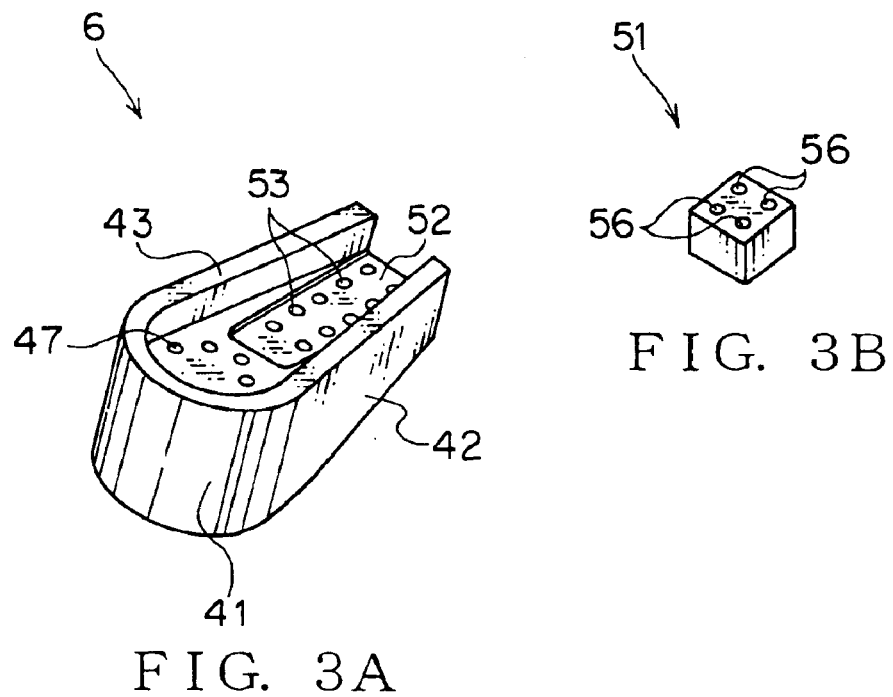
FIG. 3A
FIG. 3B
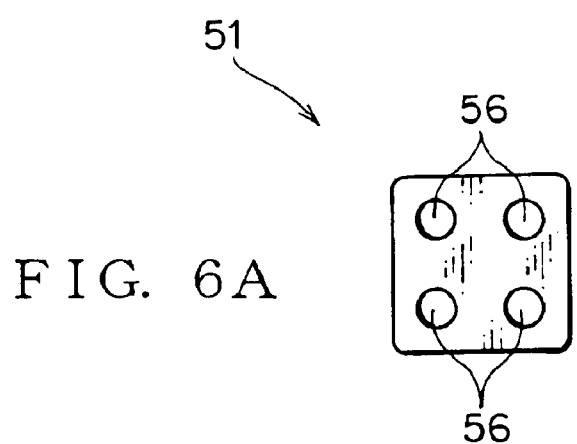
FIG. 6A
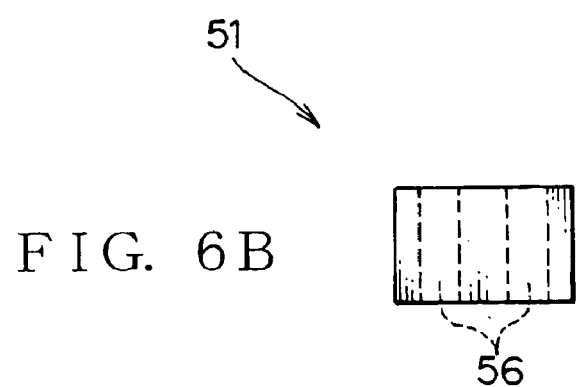
FIG. 6B

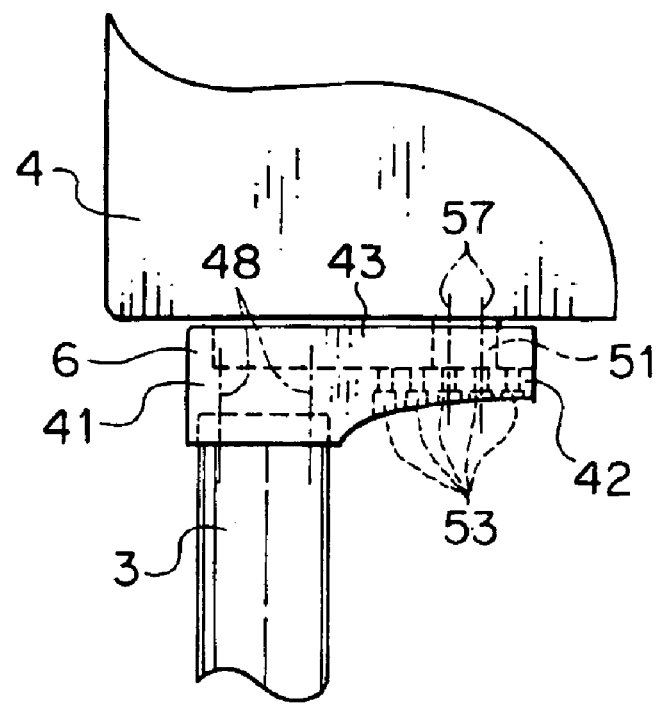
F I G. 9A
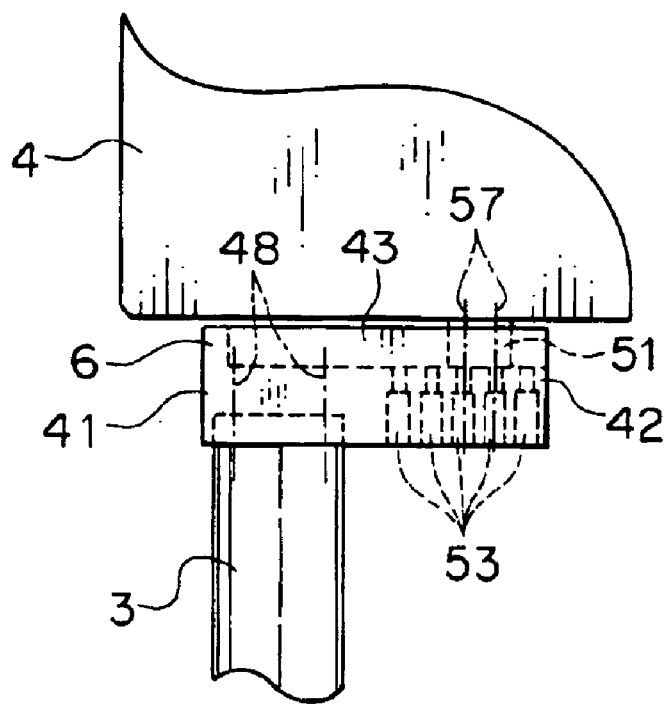
F I G. 9B

LOAD TEST MACHINE

BACKGROUND OF THE INVENTION

1. Field of the Invention

The present invention relates to a load test machine used particularly for a fatigue test to obtain a fatigue character of a test piece by applying a cyclic compression or tension load on the piece.

2. Related Art

Referring to the FIG. 10, a conventional load test machine will be explained. FIG. 10 is an illustration generally showing a conventional load test machine. The test machine has a base block 101 from which a pair of posts 103 are raised. Between the pair of the posts 103, there is a cross head 104 spanning between the posts 103. The cross head 104 is made of plates to define a hollow body. The posts 103 are jointed to the cross head 104 with bolts or the like. Furthermore, on the base block 101, there is mounted an actuator 111. Between the base block 101 and the cross head 104, a test piece 112 is removably secured to them with a pair of chucks 106. During a fatigue test, the actuator 111 applies a cyclic compression or tension load on the test piece 112. The frequency of the cyclic load is about 50 Hz.

Such a test machine is also used for obtaining a dynamic character of a rubber cushion to know an elastic constant and a damping coefficient thereof. During the test, a comparatively higher cyclic frequency is required in view of a practical use field of the rubber cushion. Thus, as disclosed in Japanese Patent Application Laid-open No. 57-48632, an air cushion is arranged between the hollow cross head and the posts to reduce the resonance frequency of the assembly to 0 (zero) to 5 Hz. An actual cyclic load frequency applied to the test is 10 to 500 Hz to obtain the elastic constant and the damping coefficient of the rubber cushion.

Conventional fatigue test machines have been generally used up to a material fatigue limit corresponding approximately to a $10^7$ cycle load. However, recently, a $10^9$ cycle load is required for obtaining a fatigue limit strength of a material used for providing a turbine construction member. It needs a load test machine allowing a higher frequency cyclic load to realize the $10^9$ cycle load in a shorter period.

The conventional load test machine is generally used for a fatigue test with about 50 Hz. This frequency takes 56 hours to complete a fatigue test of a $10^7$ cyclic load. But, it would take 232 days to complete a fatigue test of a $10^9$ cycle load. Thus, an increased frequency for a fatigue test is desired to achieve a practical shorter test period. For example, if a fatigue test frequency is changed from 50 Hz to 1,000 Hz, a fatigue test of a $10^9$ cycle load would complete in 12 days, remarkably improving its test efficiency.

The conventional load test machine has its resonance frequency higher than its test frequency, but it is practically difficult to increase the resonance frequency more than 200 Hz. To allow a 1,000 Hz frequency load, the conventional load test machine would require a constructional strength remarkably higher than a present one particularly concerning the posts 103 with a considerable increase in size and cost.

Meanwhile, a dynamic character measuring test machine uses a cyclic frequency load of 10 to 500 Hz (not of 50 Hz but up to 500 Hz) to know an elastic constant and a damping coefficient of a rubber cushion as described above. However, such test machines also are not constructed to enable a 1,000 Hz cyclic load. In the case of the conventional test machine disclosed in the laid-open application, an air cushion is provided between the posts and the cross head to achieve its lower resonance frequency of about 3 Hz. This allows a 10 to 500 Hz cyclic load but can not achieve a static load test (of about zero Hz). Furthermore, such an air cushion needs to be replaced to another one having another elasticity constant to change the resonance frequency thereof. This requires a desirable number of air cushions having elasticity constants different from each other to change the resonance frequency. Moreover, the air cushions have weights that are not easy in handling thereof, which takes an extra time to change the resonance frequency.

SUMMARY OF THE INVENTION

An object of the present invention is to provide a load test machine to eliminate the aforementioned disadvantage of the conventional art. The test machine allows a fatigue test of a higher frequency cyclic load in which its resonance frequency can be changed with ease and is also used for a static load test.

A load test machine according to the present invention includes a base block (1), at least a pair of posts (3) rising from the base block, a cross head (4) spanning between the pair of posts, and an actuator (11) mounted on the base block or the cross head. The actuator is able to apply a load on a test piece (12) positioned between the cross head and the base block. The cross head is secured to each of the posts via an elastic member (6), and the elastic member is constructed to be changeable in its jointing position with the cross head or with each of the posts to change a resonance frequency of the test machine.

The cross head may be secured to each of the posts via an elastic member made of a metal such that the elastic member is jointed to a top of each of the posts to extend laterally from the post while the cross head is jointed to an arm (42) of the elastic member.

The cross head may be jointed to the elastic member via a seat piece (51) that is changeable in its jointing position with the cross head.

The arm of the elastic member may be progressively reduced in its cross section. The arm of the elastic member may be progressively reduced in its depth. The cross head may be a solid block.

BRIEF DESCRIPTION OF THE DRAWINGS

FIG. 3A is a perspective view showing an elastic member and

FIG. 3B is a perspective view showing a seat piece;

FIGS. 4A and 4B are explanatory views showing the elastic member, FIG. 4A being a plan view, while FIG. 4B is a sectional view;

FIGS. 6A and 6B are explanatory views showing the seat piece, which are sequentially a plan view and the front view;

FIGS. 9A and 9B are explanatory views showing the elastic members each different from each other, and FIG. 9A is the front view of one elastic member having an arm with a round bottom while FIG. 9B is the front view of the other having an arm with a rectangular shape;

DETAILED DESCRIPTION OF THE PREFERRED EMBODIMENTS

Referring to FIG. 1 to 9, embodiments of a load test machine according to the present invention will be discussed.

Figure 1:
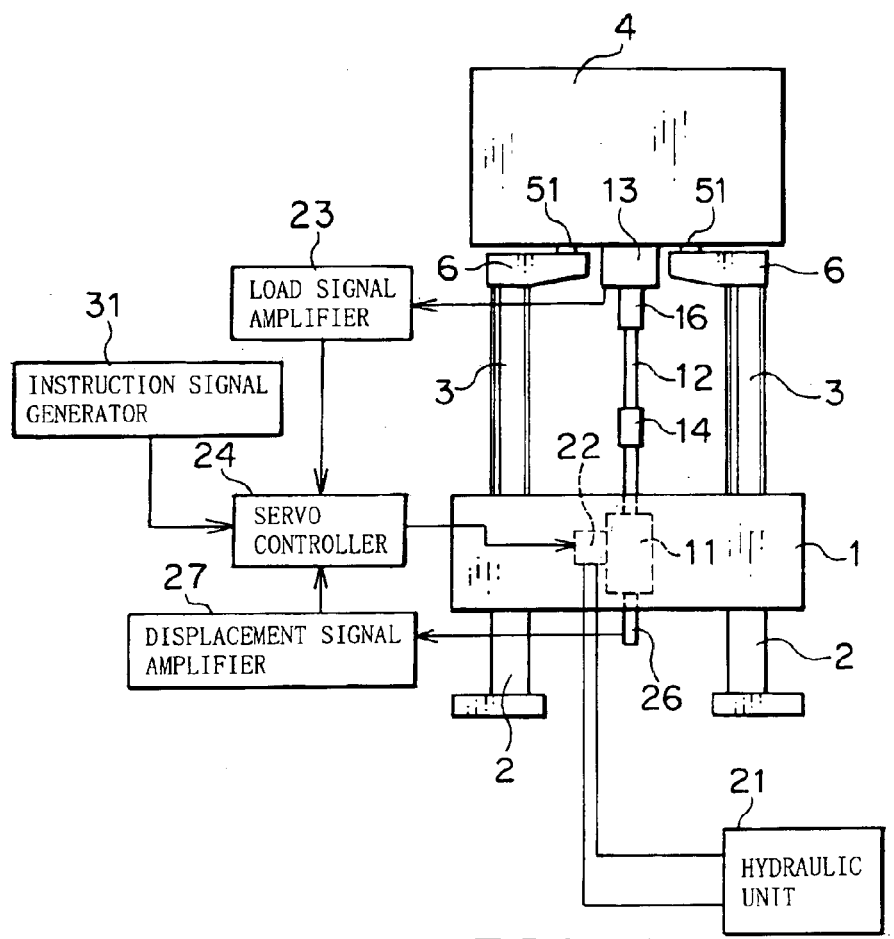
FIG. 1 is an explanatory view generally showing an embodiment of a load test machine according to the present invention.
Figure 2:
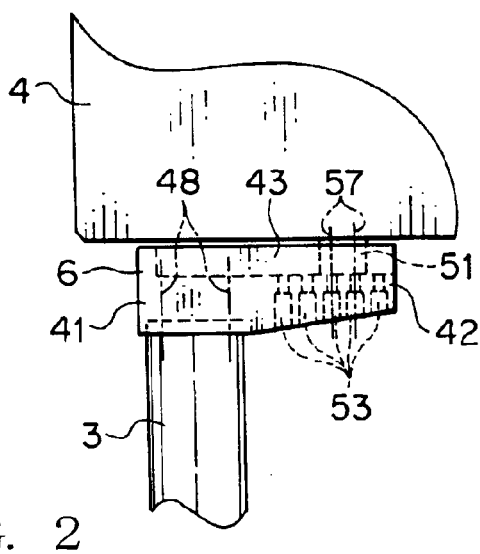
FIG. 2 is an enlarged view showing primary parts of the test machine of FIG. 1.

As illustrated in FIG. 1, the load test machine has a base block 1 that is mounted on a foundation via a plurality of legs 2. On the base block 1, a pair of posts 3 stands, and a cross head 4 is provided to cross over the pair of the posts 3. The cross head 4 is defined in a solid metal block and secured to a top of each post 3 via a metal elastic member (elastic beam or bracket) 6. That is, the cross head 4 does not join directly to the posts 3 but resiliently joints to the posts 3 through the elastic members 6. The elastic member 6 will be discussed later in detail. On the base block 1, there is mounted a hydraulic actuator 11 having an actuating rod that is removably coupled to a test piece 12 by a lower chuck 14. Meanwhile, on the cross head 4, there is provided a load cell 13 for measuring a load applied on the test piece 12. The test piece 12 is removably attached to a bottom of the cross head 12 by an upper chuck 16. Thus, the test piece 12 is removably secured between the base block 1 and the cross head 4 so that the actuator 11 can load on the test piece 12.

The actuator 11 receives a pressurized oil from a hydraulic unit 21 having a hydraulic pump through a servo valve 22. The load cell 13 measures a load to output a signal corresponding to the load to a servo controller 24 via a load signal amplifier 23. The displacement of the rod of the actuator 11 (i.e., the displacement of the lower end of the test piece 12) is measured by a displacement gauge 26, and the measured data is supplied to the servo controller 24 through a displacement signal amplifier 27. The servo controller 24 electrically connects to an instruction signal generator 31 outputting instruction signals to control the displacement of the rod or the value of the load. The servo controller 24 outputs operational signals to the servo valve 22 to make a feed-back control based on the load value measured by the load cell 13 or the displacement signal obtained by the displacement gauge 26 which corresponds to the instruction signal generated by the instruction signal generator 31. In a fatigue test, the instruction signal generator 31 outputs cyclic signals, for example, of a sin wave form to apply cyclic compression or/and tension loads to the test piece 12.

The elastic member 6 is made of a metal and has a post coupling portion 41 and an arm 42 extending laterally from the post coupling portion 41 (rightward or leftward as shown in FIG. 1). The post coupling portion 41 is secured to a top of the post 3 and defined in a generally circular shape in a plan view. The elastic member 6 has a vertical peripheral wall 43 except its extension end. The post coupling portion 41 has a bottom surface formed with an engagement recess 46 receiving the top of the post 3. In the recess 46, the post coupling portion 41 is formed with a plurality of bolt through holes 47 to secure the post 3 with bolts. The post 3 has a plurality of threaded bolt holes (not shown) associated with the bolt through holes 47. The bolts joint the post 3 with the elastic member 6 along chain lines 48.

Figure 4A:
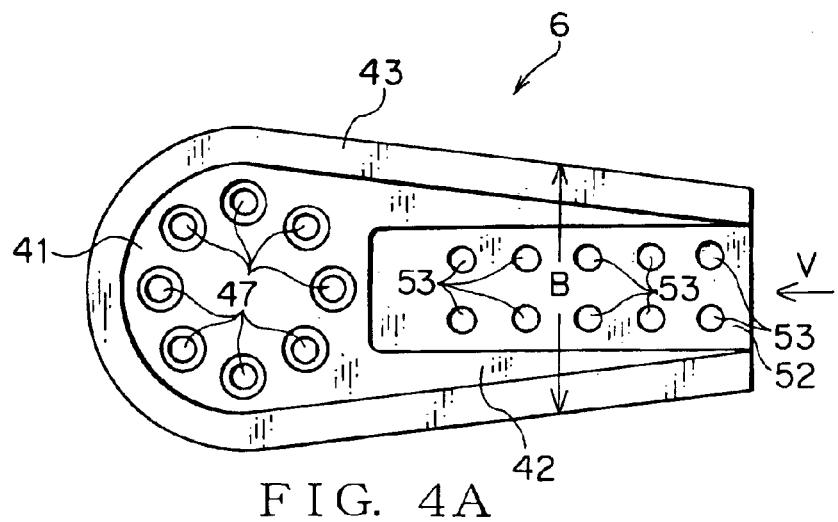
Figure 4B:
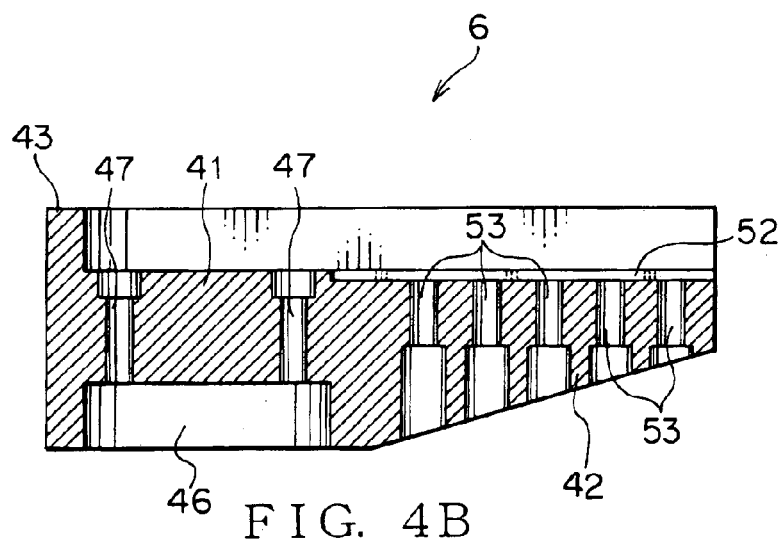
Figure 5:
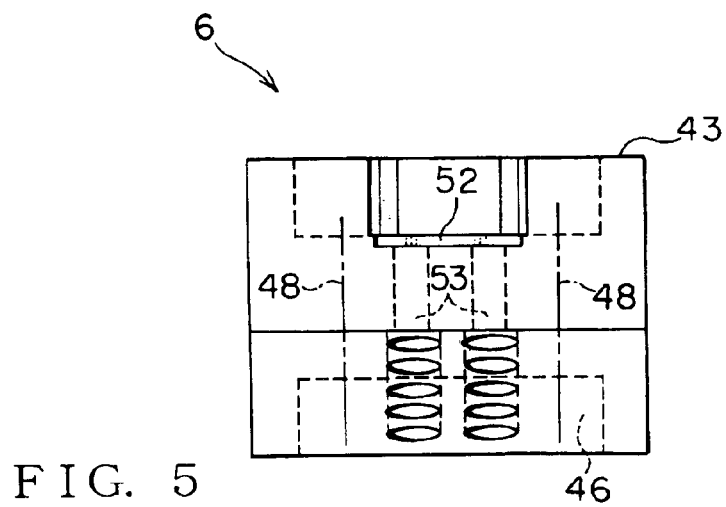
FIG. 5 is a side view taken along an arrowhead V of FIG. 4A.

The arm 42 has a guide recess 52 slidingly guiding a seat piece 51 in its upper surface in an extending direction of the arm 42. The arm 42 is formed with a plurality (ten in the embodiment) of bolt through holes 53. The arm 42 is progressively reduced in cross section area. That is, the arm 42 has a horizontal top surface and a bottom surface inclined upward, gradually reducing it depth in the extension direction. The arm 42 has a progressively smaller width B as shown in FIG. 4A.

As illustrated in FIG. 6, the seat piece 51 of this embodiment is formed with four bolt through holes 56. The cross head 4 has a bottom surface formed with bolting holes (not shown) aligned with associated bolt through holes 53 of the arm 42 of the elastic member 6. The cross head 4 is bolted to the elastic member 6 via the seat piece 51, in which four of the bolt through holes 53 are used while the other elastic member 6 holes are not used. The case shown in FIG. 2 uses the second and third ones of the bolt through holes 53 in a leftward direction of the drawing. The bolts are inserted upward through the bolt holes 53 of the arm 42 and the bolt through holes 56 of the seat piece 51 along to chain lines 57 to be screwed into the bolt holes of the cross head 4, so that the bolting secures the cross head 4 to the elastic member 6 via the seat piece 51.

The seat piece 51 is changeable in its securing position so that the jointing position of the seat piece 51 to the cross head 4 with the bolts can be changed. The embodiment allows four jointing positions. The displacement of the jointing position alters the elasticity constant of the elastic member 6. The jointing position nearer to the root of the arm 42 achieves the larger elasticity constant. As shown by an arrowhead of FIG. 8, a resonance frequency of the whole load test machine displaces rightward to become larger. The resonance frequency varies primarily with the weight of the cross head 4 and the elastic constant of the elastic member 6. The resonance frequency decreases with increase of the cross head weight and increases with increase of the elastic constant of the elastic member 6.

FIGS. 9A and 9B show modified examples of the elastic member 6. A first modified example illustrated in FIG. 9A has an arm 42 with a round bottom, while a second modified example illustrated in FIG. 9B has a rectangular arm 42 with a generally horizontal bottom surface.

Figure 8:
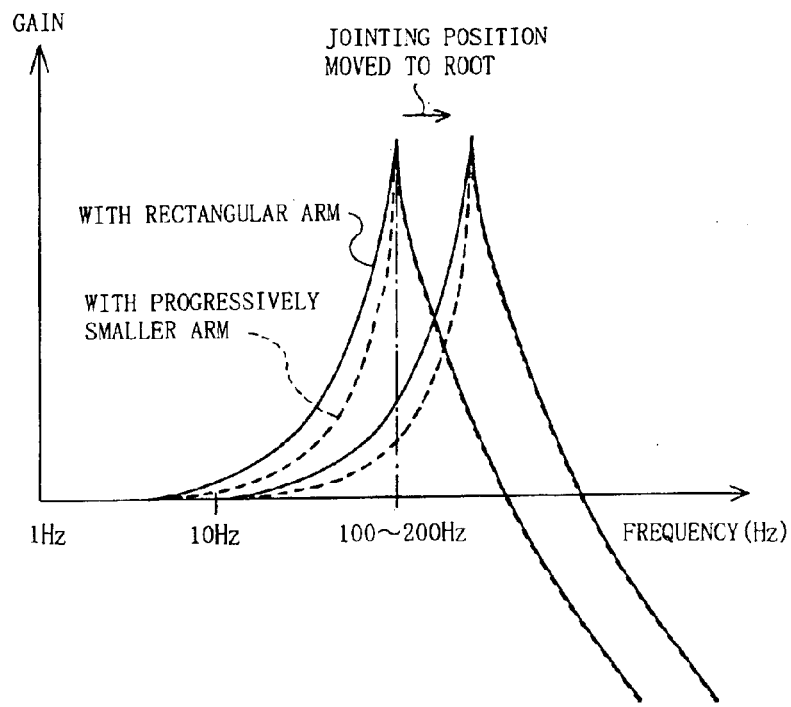
FIG. 8 is a graph showing relationships between test cyclic frequencies and gains of the test machine.
Figure 11:
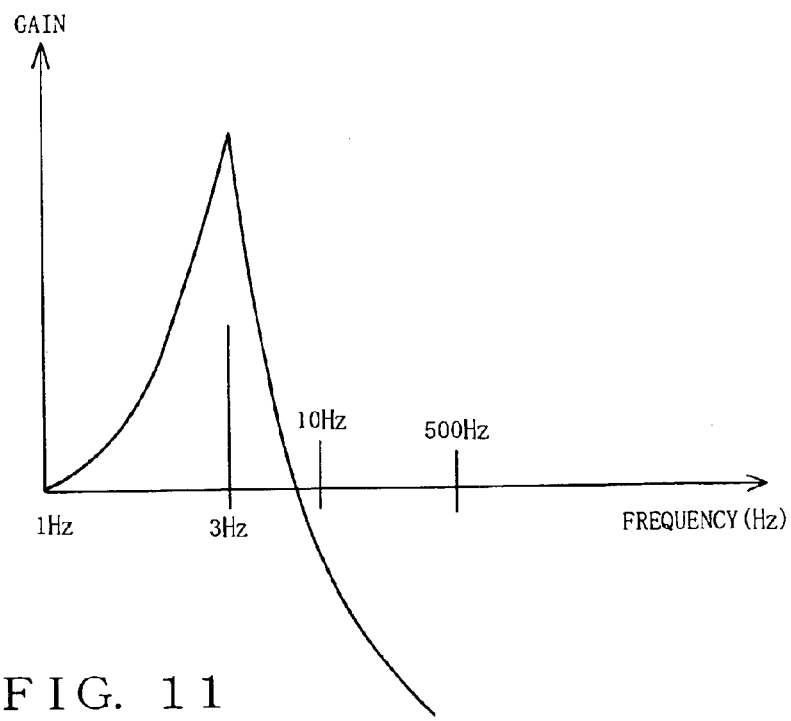
FIG. 11 is a graph showing relationships between test cyclic frequencies and gains of a dynamic character measurement test machine having an air cushion.
Figure 10:
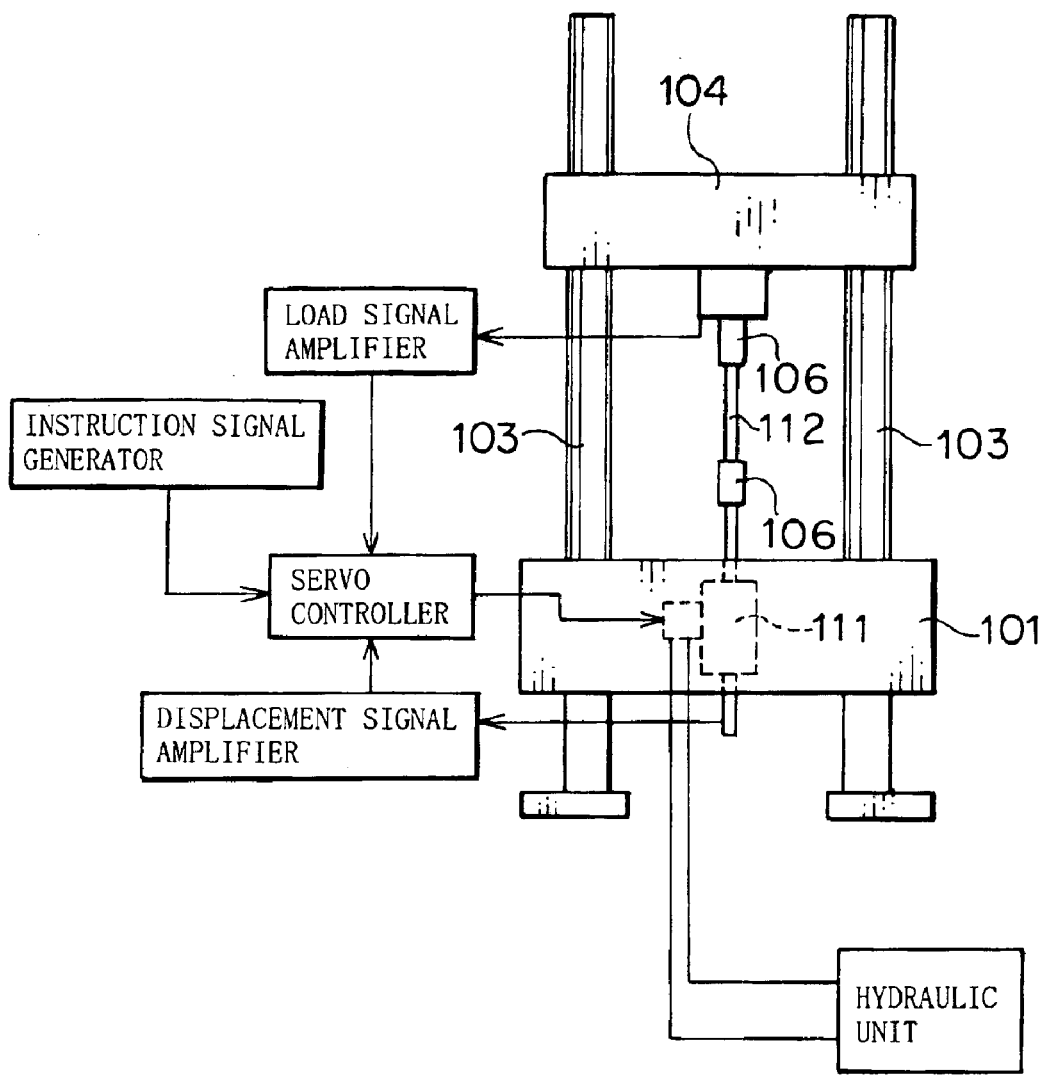
FIG. 10 is an illustration generally showing a conventional load test machine.

Thus configured load test machine includes the elastic members 6 having an elastic constant larger than that of a conventional air cushion, so that the resonance frequency of the load test machine can be 100 to 200 Hz as illustrated in FIG. 8. Thus, the load test machine allows a static load test with a nearly zero load frequency.

Figure 7:
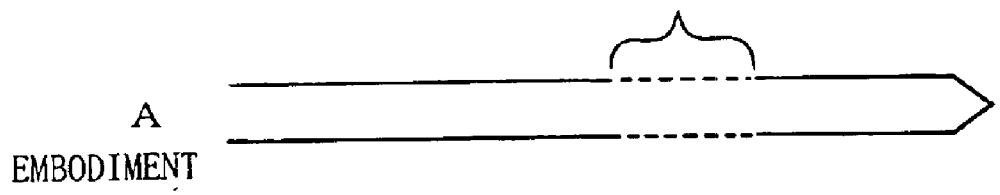
FIG. 7 is an explanatory view showing cyclic load frequencies applicable to the test machine.
Figure 7:
Figure 7:
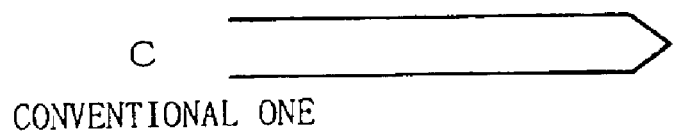
Figure 7:
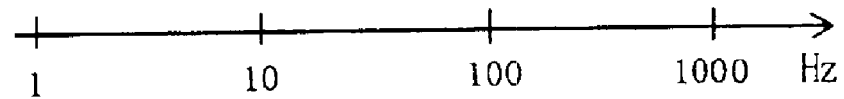

Furthermore, the elastic constant of the elastic member 6 varies with the jointing position of the elastic member 6 and the cross head 4. Thus, the resonance frequency of the test machine is adjustable to enable a cyclic load frequency used for a fatigue test. FIG. 7 shows allowable ranges of cyclic load frequencies. Reference marks A, B, and C designate sequentially allowable ranges of the discussed embodiment, a load test machine with an air cushion, and the conventional test machine. In the embodiment, the load test machine has a resonance frequency of 100 to 200 Hz, but a broad range of test load frequencies is allowable as designated by mark A by varying the jointing position of the cross head 4 with the elastic member 6 to change the resonance frequency of the test machine. For example, when the test machine has the resonance frequency of 150 Hz, an allowable test frequency is smaller than 100 Hz or larger than 200 Hz. When the test machine has the resonance frequency of 100 Hz, an allowable test frequency becomes smaller than 50 Hz or larger than 150 Hz. Meanwhile, when the test machine has a higher resonance frequency of 200 Hz, an allowable test frequency becomes smaller than 150 Hz or larger than 250 Hz.

On the contrary, a load test machine with an air cushion has a lower resonance frequency because of a smaller elastic constant of the air cushion, so that a static load test or a load test with a considerably low frequency of nearly zero is not applicable to the test machine as shown by mark B in FIG. 7. The conventional test machine allows only a load frequency not more than 100 Hz and can not be applicable to a fatigue test with a higher frequency as shown by mark C in FIG. 7.

The test machine of the embodiment has a resonance frequency changed by altering the jointing position of the cross head 4 and the elastic member 6, which does not require another elastic member 6, reducing the number of parts of the test machine. The seat piece 51 can be easily moved to change the jointing position. The elastic member 6 has the upper surface formed with the guide recess 52 along which the seat piece 51 is slidingly displaced to change its jointing position with ease.

In FIG. 8 that shows graphs of relationships between load frequencies and gains. Curves of solid lines are associated with FIG. 9B in which the arm 42 of the elastic member 6 is generally rectangular, while curves of dotted lines are associated with FIG. 2 in which the arm 42 of the elastic member 6 is progressively smaller. The graphs of FIG. 8 show that the progressively smaller arm 42 is better to reduce an effect of the resonance of the test machine when the cyclic load test uses a frequency around the resonance frequency. In addition, it is more advantageous for reducing the resonance effect that the arm 42 has a progressively smaller depth than a progressively smaller width.

The cross head 4 defined in a solid metal block allows a maximum solidity to provide a higher natural frequency of the cross head 4, for example, about 1,500 Hz that is higher than a usual test frequency. This prevents the cross head 4 itself from resonating with a test cyclic load.

In addition, at least a pair of the posts 3 are provided for the test machine, and the provision of four of them maybe practical. The hydraulic actuator may be replaced by another type one. The actuator may be arranged not on the base block 1 but on the cross head 4.

The jointing structure between the elastic member 6 and the post 3 or between the elastic member 6 and cross head 4 may be configured in another way. For example, the bolting may be replaced by another securing means. The elastic member 6 may be altered in shape and material. Furthermore, the bolt through holes 53 and the jointing positions may be adequately altered in number.

In the discussed embodiment, the jointing position of the elastic member 6 with the cross head 4 is changeable. Alternatively, the jointing position of the elastic member 6 with the post 3 may be constructed to be changeable. However, the former configuration of the jointing position is easier than the latter in construction.

The load test machine can be used for a load test other than a fatigue measurement. The progressively smaller arm 42 may have a progressively smaller depth or width. The progressively smaller depth is more advantageous than the progressively smaller width. Now, advantageous effects of the present invention will be summarized. According to the present invention, the jointing position of the elastic member with the cross head or of the elastic member with post is changeable, so that the resonance frequency of the test machine is adjustable. Thus, it is possible that the elastic member is positioned such that the resonance frequency becomes about 100 to 200 Hz to allow a cyclic load frequency of 1,000 Hz for a fatigue test. When the resonance frequency disturbs a load wave form, the jointing position of the elastic member is changed to alter the resonance frequency to correct the wave form to obtain a precise test result.

The elastic member made of a metal and extended laterally from the post can have an elastic constant larger than that of an air cushion to provide a higher resonance frequency. The elastic member 6 is easy to change the jointing position with the cross head. This allows a static load test and a low frequency cyclic test in addition to an easy adjustment of the resonance frequency of the test machine.

The cross head jointed to the elastic member via the seat piece adjustable in position can easily change the resonance frequency of the test machine.

The elastic member has the progressively smaller arm that reduces an effect of the resonance frequency when a load frequency is near the resonance frequency.

The cross head defined in a solid metal block allows a maximum solidity to provide a higher natural frequency of the cross head 4, for example, about 1,500 Hz that is higher than a usual test frequency of 1,000 Hz. This prevents the cross head itself from resonating with a test cyclic load, improving the test in precision.

What is claimed is:

1. A load test machine comprising:
    a base block,
    at least a pair of posts rising from the base block,
    a cross head spanning between the pair of posts, and
    an actuator mounted on the base block or the cross head, the actuator being able to apply a load on a test piece positioned between the cross head and the base block,
    wherein the cross head is secured to each of the posts via an elastic member, and the elastic member is constructed to be changeable in its jointing position with the cross head or with each of the posts to vary an elastic constant of the elastic member to change a resonance frequency of the test machine.

2. The load test machine as recited in claim 1 wherein the cross head is a solid block.

3. A load test machine comprising:
    a base block,
    at least a pair of posts rising from the base block,
    a cross head spanning between the pair of posts, and
    an actuator mounted on the base block or the cross head, the actuator being able to apply a load on a test piece positioned between the cross head and the base block,
    wherein the cross head is secured to each of the posts via an elastic member made of a metal such that the elastic member is jointed to a top of each of the posts to extend laterally from the post to define an arm while the cross head is jointed to the arm of the elastic member, the elastic member being changeable in its jointing position with the cross head to vary an elastic constant of the elastic member to change a resonance frequency of the test machine.

4. The load test machine as recited in claim 3 wherein the arm of the elastic member is progressively reduced in its cross section.

5. The load test machine as recited in claim 4 wherein the arm of the elastic member is progressively reduced in its depth.

6. The load test machine as recited in any one of claims 3 to 5 wherein the cross head is a solid block.

7. A load test machine comprising:
a base block,
at least a pair of posts rising from the base block,
a cross head spanning between the pair of posts, and
an actuator mounted on the base block or the cross head, the actuator being able to apply a load on a test piece positioned between the cross head and the base block,
wherein the cross head is secured to each of the posts via an elastic member made of a metal such that the elastic member is jointed to a top of each of the posts to extend laterally from the post to define an arm while the cross head is jointed to the arm of the elastic member via a seat piece, the seat piece being changeable in its jointing position with the cross head.

8. The load test machine as recited in claim 7 wherein the arm of the elastic member is progressively reduced in its cross section.

9. The load test machine as recited in claim 8 wherein the arm of the elastic member is progressively reduced in its depth.

10. The load test machine as recited in any one of claims 7 to 9 wherein the cross head is a solid block.

11. The load test machine recited in claim 1, wherein the elastic member is constructed to be changeable in its jointing position with the cross head.

12. The load test machine recited in claim 11, wherein the elastic member is formed with a plurality of bolt holes that are partially used for bolt-jointing the elastic member with the cross head to change the jointing position.

* * * * *